(12) United States Patent
Katsuki et al.

(10) Patent No.: US 6,916,410 B2
(45) Date of Patent: Jul. 12, 2005

(54) BIOSENSOR

(75) Inventors: Koji Katsuki, Kyoto (JP); Katsumi Hamamoto, Kyoto (JP); Yuji Yagi, Kyoto (JP); Takao Fukuoka, Kyoto (JP)

(73) Assignee: Arkray, Inc., Kyoto (JP)

( * ) Notice: Subject to any disclaimer, the term of this patent is extended or adjusted under 35 U.S.C. 154(b) by 359 days.

(21) Appl. No.: 10/147,213

(22) Filed: May 15, 2002

(65) Prior Publication Data

US 2002/0189941 A1 Dec. 19, 2002

(30) Foreign Application Priority Data

Nov. 15, 1999 (JP) ............................................. 11-361450

(51) Int. Cl.$^7$ ............................................. G01N 27/327
(52) U.S. Cl. ........................... 204/403.05; 204/403.01; 204/403.14
(58) Field of Search ........................ 204/403.01, 403.06, 204/403.1, 403.11, 403.14, 409

(56) References Cited

U.S. PATENT DOCUMENTS

| 5,643,721 A | 7/1997 | Spring et al. ................... 435/6 |
| 5,770,028 A | 6/1998 | Maley et al. ........... 204/403.11 |
| 6,627,057 B1 * | 9/2003 | Bhullar et al. ......... 204/403.01 |

FOREIGN PATENT DOCUMENTS

| EP | 0 267 724 | 5/1988 | .......... G01N/33/52 |
| EP | 0 840 124 A2 | 5/1998 | .......... G01N/33/52 |
| EP | 0859229 A1 * | 8/1998 | .......... G01N/27/327 |
| JP | 2-221855 A | 9/1990 | .......... G01N/27/327 |
| JP | 03160358 A * | 7/1991 | .......... G01N/27/327 |
| JP | 03170854 A * | 7/1991 | .......... G01N/27/32 |
| JP | 4-295755 A | 10/1992 | .......... G01N/27/327 |
| JP | 5-164725 A | 6/1993 | .......... G01N/27/327 |
| JP | 9-80010 A | 3/1997 | .......... G01N/27/327 |
| JP | 10-113200 A | 5/1998 | ............ C12Q/1/25 |
| JP | 10-132750 | 5/1998 | .......... G01N/27/78 |
| WO | 94/24262 | 10/1994 | |
| WO | 98/35053 | 8/1998 | ............ C12Q/1/00 |
| WO | 99/22227 | 5/1999 | .......... G01N/27/00 |

OTHER PUBLICATIONS

Derwent abstract of JP 0310854 A (New Japan Radio Co. Ltd.).*
JPO abstract of JP 03160358 A (Koichi Okuma).*
Derwent abstract of JP 05–164725 A (Toto Ltd.).*
Poyard S et al.:"A new method for the controlled immobilization of enzyme in inorganic gels (laponite) for amperometric glucose biosensing" Sensors and Actuators B, Elsevier Sequoia S.A., Lausanne, CH, vol. 33, No. 1, Jul. 1, 1996, pp. 44–49, XP004013040 ISSN: 09254005.
J.L. Besombes, S. Consnier & P. Labbe: "Improvement of poly(amphiphilic pyrrole) enzyme electrode via the incorporation of synthetic laponite–clay–nanoparticles" TALANTA, vol. 44, 1997, pp. 2209–2215, XP002219540.

(Continued)

*Primary Examiner*—Alex Noguerola
(74) *Attorney, Agent, or Firm*—Merchant & Gould P.C.

(57) ABSTRACT

A biosensor is constituted by disposing an electrode system including a working electrode and a counter electrode on a substrate, forming an inorganic particulate-containing layer containing inorganic particulates thereon, and forming a reagent layer containing a reagent thereon. The inorganic particulates make it possible to prevent impurities in a sample from being in contact with the electrode system and being adsorbed therein, so that measurement is performed with high precision. The inorganic particulate-containing layer can be formed by applying a dispersion system of inorganic particulates and drying them, and it is preferable that the inorganic particulates are contained in the form of aggregates.

20 Claims, 5 Drawing Sheet

OTHER PUBLICATIONS

S. Sampath & O. Lev: "Membrane–free, rhodium–modified, methyl silicate–graphite amperometric biosensor" Journal of Electroanalytical Chemistry, vol. 426, 1997, pp. 131–137, XP002219541.

Consier Serge et al.: "A composite clay glucose biosensor based on an electrically connected HRP." Electroanalysis, vol. 12, No. 5, Mar. 2000, pp. 356–360, XP009000235 ISSN: 1040–0397.

* cited by examiner s

BIOSENSOR

This application is the national stage under 35 U.S.C. 371 of PCT/JP00/08029, which was filed on Nov. 14, 2000.

TECHNICAL FIELD

The present invention relates to a biosensor for electrochemically measuring a specific component in a sample liquid such as blood.

BACKGROUND ART

Biosensors that can quantify a specific object to be measured in a sample liquid in a simple and rapid manner, for example, without diluting or stirring the sample liquid have been used widely. Such a biosensor can be produced by, for example, forming an electrode system having a working electrode (also referred to as "measuring electrode") and a counter electrode on an electrically insulating substrate by a method such as screen printing, and forming a reactive layer including a redox (oxidation-reduction) enzyme and an electron-accepting substance that react with the objective to be measured thereon. When the reactive layer is in contact with the sample liquid containing the object to be measured, the object to be measured is oxidized by the catalytic action of the redox enzyme, and the electron-accepting substance is reduced at the same time. The reduced electron-accepting substance is re-oxidized by an electrochemical approach, and the concentration of the object to be measured in the sample liquid can be calculated from the thus obtained oxidation current values.

However, there may be errors in the measurement, depending on the properties of the sample liquid or the like. Possible reasons for this are as follows. For example, a whole blood sample contains impurities, for example, solid matter such as blood cells, soluble components such as lipid, protein, and saccharides, and insoluble components. The area of the surface of the electrodes may be decreased by the adsorption of these impurities onto the surface of the electrodes, or the impurities may hinder the diffusion of the reagent and inhibit the enzyme reaction. Consequently, the current value is decreased. Furthermore, there is a large difference between individuals in the hematocrit (Hct) value, which is a volume ratio of erythrocytes to whole blood, so that there is a difference between specimens in the above-described influence on the biosensor. Such an influence due to the impurities can be decreased by, for example, diluting the sample liquid and then subjecting the diluted sample liquid to a biosensor. However, this takes more time and complicates the operation.

In order to avoid such an influence, the following biosensors have been proposed: a biosensor (JP9-80010 A) in which an immobilized enzyme film containing mutually charge-coupled redox enzymes and chitosan is disposed on a detection surface of the electrode system; and a biosensor (IP10-113200 A) in which a layer comprising microparticles of a water-soluble high molecular weight compound and conductive particulates is disposed. The microparticles contain an enzyme. These biosensors attempt to decrease the influence due to the impurities by providing the above-described various layers as a filtering film, and bringing the sample liquid into contact with the electrode surface via the filtering film to suppress the impurities in the sample liquid from coming close to the electrode surface.

Such a biosensor can filtrate impurities such as erythrocytes or proteins that hinder measurement. However, since the filtering film is provided, the permeation of the sample liquid is not uniform, so that the electrode surface may not become sufficiently wet. Therefore, for example, air bubbles remain on the electrodes, so that an effective measurement area of the electrodes is decreased, which may cause measurement errors. Furthermore, the permeation of the sample liquid takes time, and therefore the response speed is slow.

DISCLOSURE OF INVENTION

In order to avoid these problems, another biosensor (JP7-107525 B) in which a layer made of a hydrophilic high molecular weight compound, such as starch-based, carboxy methyl cellulose (CMC)-based, gelatin-based compounds, is provided has been proposed.

In this biosensor, the problem with the filtering film is solved, but since a water-soluble high molecular weight compound is used, the water absorptivity is high so that the biosensor is susceptible to humidity, which causes problems in that the enzyme reaction is slow or the form of the layer is unstable. Therefore, it is difficult to improve measurement precision, and measurement takes time.

Therefore, it is an object of the present invention to provide a biosensor that can measure an object to be measured in a sample rapidly and simply with high precision without being affected by the impurities in the sample.

In order to solve the above problems, a biosensor of the present invention includes a substrate, a reagent layer containing a reagent, and an electrode system including a working electrode and a counter electrode, the electrode system being disposed on the substrate, and the reagent layer being formed on the electrode system, wherein the reagent layer further comprises inorganic particulates.

As a result of in-depth research, the inventors of the present invention found out, based on the following findings, that the impurities can be prevented from becoming attached to the electrodes by forming on the electrodes a layer that is turned into a gel or a sol by a sample liquid permeating the layer.

It is known that the above-described hydrophilic high molecular weight compound, in general, is turned into a gel or a sol by absorbing water. However, in a biosensor, when a layer containing the hydrophilic high molecular weight compound is formed, it takes time for a sample liquid to permeate this layer so that water molecules in the sample liquid swell the high molecular weight compound and turn it into a gel. In other words, the water molecules have to permeate a high molecular weight structure in which long principal chains are intertwined. Since this involves the movement of the principal chains, this is thermodynamically disadvantageous, compared with when a low molecular weight compound is dissolved in water. Therefore, it takes time for the layer to be turned into a gel layer or the like that is suitable for measurement by being swollen. As a result, the time required for measurement also tends to be long. In addition, the hydrophilic high molecular weight compound of some kinds may be dissolved partially by a contact with a liquid, and thus the composition of a sample liquid may change or impurities cannot sufficiently be prevented from being adsorbed in the electrodes. These phenomena generally can occur, regardless of whether the hydrophilic high molecular weight compound is derived from natural substances or synthesized products.

Then, as a result of further research, the inventors of the present invention found out that inorganic particulates are swollen easily by the permeation of the sample liquid, so that impurities are prevented from passing through the reagent layer by letting the reagent layer contain the inorganic particulates, and are prevented from becoming attached to the electrode surface. Furthermore, the inorganic particulates are not susceptible to the influence of humidity as described above. Therefore, the sensitivity is prevented from deteriorating, regardless of the properties of the sample, such as the hematocrit value in the blood, and measurement can be performed easily, rapidly and highly precisely.

In the biosensor of the present invention, the reagent layer may be a single layer or a laminate comprising a reagent-containing layer containing the reagent and an inorganic particulate-containing layer containing the inorganic particulates.

In the case where the reagent layer is the laminate, the inorganic particulate-containing layer may be formed on the electrode system via the reagent-containing layer, but it is preferable that the reagent-containing layer is formed on the electrode system via the inorganic particulate-containing layer, because the adsorption of the impurities onto the electrodes can further be eliminated, for example.

In the present invention, it is preferable that the reagent layer contains aggregates of inorganic particulates. If the inorganic particulates are in the form of aggregates, impurities such as erythrocytes can be prevented more effectively from passing through the reagent layer by interaction of the particulates.

Furthermore, it is preferable that a layer containing inorganic particulates (the reagent layer or inorganic particulate-containing layer) is formed by applying a dispersion system in which the inorganic particulates are dispersed on the electrode system, and drying the dispersion system. The dispersion system may be in the form of a gel or a sol, for example. The layer formed in this manner has a structure including aggregates of particulates, and it seems that the layer becomes a gel or a sol again by the permeation of the sample liquid through the layer and the swelling of the particulates by water molecules. The inorganic particulates can easily be dispersed in a dispersion medium such as water, so that a dispersion system having a suitable concentration is prepared as appropriate, and is applied onto the electrode system and dried, and thus a thin film having a necessary thickness can be formed easily.

In the present invention, it is preferable that the content of the particulates in the reagent layer or the layer containing the particulates is in the range from 0.14 to 14.0 mg per $cm^2$ of the area, and it is preferable that the thickness of the layer is in the range from 0.05 to 3 $\mu$m.

It is preferable that the inorganic particulates are expansive particulates for the above-described reason. It also is preferable that the inorganic particulates are particulates of clay mineral. For example, expansive phyllosilicate can be used, and smectite, expansive mica and the like are preferable. Preferable examples of the smectite include hectorite, saponite, and montmorillonite, and preferable examples of the expansive mica include sodium tetrasilicon fluoride mica and teniorite. These inorganic particulates can be used alone or in combination with two or more kinds.

As the smectite, for example, a product named Labonight XLG and a product named Labonight XLS (both manufactured by Laboat Industries Co. Ltd.), a product named Lucentite SWN and a product named Lucentite SWF (manufactured by CO-OP CHEMICAL Co. Ltd.) and a product named Chikisopi W (manufactured by Kyowa Chemical Industry Co., Ltd., which are commercially available hectorite, a product named Smecton SA (Kunimine Industries, Co. Ltd.), which is a commercially available synthesized saponite, a product named Kunipia F (Kunimine Industries, Co. Ltd.), which is a commercially available natural montmorillonite purified product or the like can be used.

As the expansive mica, for example, a product named Na-TS (TOPY INDUSTRIES LIMITED), which is a commercially available sodium tetrasilicon fluoride mica, a product named Li-TN (TOPY INDUSTRIES LIMITED), which is a commercially available teniorite or the like can be used.

In the biosensor of the present invention, it is preferable that the reagent layer further comprises particulates of a water-insoluble high molecular weight compound (hereinafter, referred to as "water-insoluble particulates"). This water-insoluble particulate makes it possible to prevent the impurities in the sample from becoming attached onto the electrodes. Also in this case, the reagent layer may be a single layer or a laminate. In the case of a laminate, it is preferable that the water-insoluble particulates are contained in the reagent-containing layer, although not limited thereto.

Furthermore, a water-insoluble particulate-containing layer containing the water-insoluble particulates may be further included. In this case, the reagent layer may be formed on the electrodes via the particulate-containing layer, but it is preferable that the water-insoluble particulate-containing layer is formed on the electrodes via the reagent layer, because, for example, the adsorption of the impurities onto the electrodes can be further avoided, and the object to be measured in the sample and the reagent can react with each other easily.

In the biosensor of the present invention, the water-insoluble high molecular weight compound does not contain impurities that causes electrolysis and is electrochemically inactive. More specifically, a polymer or a copolymer containing at least one of acrylic acid, methacrylic acid, maleic acid, acrylic ester, methacrylic acid ester, maleic acid ester, styrene, and a styrene derivative monomer can be used. An example of the styrene derivative monomer is styrene or alkylstyrene. In addition, urethane compounds such as polyurethane and polyurea, polyolefin high molecular weight compounds such as polyethylene and polypropylene, polyolefin derivatives such as polyvinyl chloride, polyamide compounds and the like can be used. In addition to the high molecular weight compounds as described above, inorganic compounds such as ceramics typified by silica gel, alumina, zeolite, apatite, glass, and alite can be used. Among these, a polymer or a copolymer containing at least one of acrylic acid, methacrylic acid, maleic acid, acrylic ester, methacrylic acid ester, maleic acid ester, and a styrene derivative monomer, or a polyamide-based high molecular weight compound are preferable, because they are electrochemically inactive. More specifically, polymethacrylic acid, PMMA, polystyrene (PS), polyamide (PA) and the like are particularly preferable.

Suitable water-insoluble particulates include a commercially available product named Techpolymer bmx-5 (manufactured by SEKISUI PLASTICS Co., Ltd., PMMA, spherical, a particle diameter 5 $\mu$m), a product named Ganzpearl GM-0600 (manufactured by Ganz Kasei Co. Ltd., PMMA, spherical, a particle diameter 6 $\mu$m), a product named Ganzpearl GS-0805 (manufactured by Ganz Kasei Co. Ltd., PMMA, crosslinked PS, a particle diameter 8 $\mu$m), a product named Ganzpearl PS-8F (manufactured by Ganz Kasei Co. Ltd., PMMA, spherical, a particle diameter 0.4 $\mu$m), a product named Orgasol 2002EXD NAT COS TypeS (manufactured by Elfatchem Co. Ltd., nylon, spheroidal, a size 10 μm), a product named Trefil E-506C (manufactured by TORAY DOW CORNING SILICONE CO., Ltd., crosslinked silicone, spherical, a particle diameter 10 μm), a product named Saramics SN-E-02 (manufactured by UBE INDUSTRIES, LTD., silicon nitride, spherical, a particle size 1 μm), a product named Gotball (manufactured by SUZUKI OIL & FATS CO., LTD., silica, spherical, a particle size 10 μm), a product named Glassbeads (manufactured by Polysciences, Inc., lime glass, spherical, a particle size 3 to 10 μm), or the like.

The average particle diameter of the water-insoluble particulates is in the range from 0.1 to 45 μm, preferably 0.5 to 30 μm, more preferably 1 to 20 μm, and particularly preferably 3 to 15 μm. If the average particle diameter is 0.1 μm or more, it is easy for a sample to permeate the reagent layer sufficiently and the sensitivity of the biosensor can be improved. If the average particle diameter is 45 μm or less, the influence of the impurities in the sample can be eliminated sufficiently.

The average particle diameter can be obtained by, for example, observing directly the water-insoluble particulates through an electron microscope and measuring the particle diameter to calculate the average. There is no limitation regarding the number of the particulates to be measured, but for example, the number is 100 or more, and preferably in the range from 100 to 300.

There is no limitation regarding the particle size distribution of the water-insoluble particulates, but preferably, it is in the range from 0.01 to 100 μm, more preferably 0.05 to 60 μm, and particularly preferably 0.1 to 40 μm.

As the water-insoluble particulates, spherical or spheroidal particulates, or a spherical aggregate of particulates can be used, but it is preferable that spherical particulates are used, because the layer containing the water-insoluble particulates can be uniform and retain an appropriate density.

Furthermore, it is preferable that the water-insoluble particulates are electrically inactive, and it is preferable to change the particle diameter in accordance with the impurities to be removed, and to change the characteristics of the surface of the particulates. For example, when it is desired to change the characteristics of the surface of the water-insoluble particulates to be hydrophobic, it is preferable to use particulates formed of PS. When it is desired to change the characteristics to be more hydrophilic than PS, it is preferable to use particulates formed of PMMA, PA or the like. Furthermore, when it is desired to change the characteristics to be negatively charged, it is preferable to use particulates formed of PS or the like to which a carboxyl group is introduced. When it is desired to change the characteristics to be positively charged, it is preferable to use particulates formed of PS or the like to which an amino group is introduced.

In the biosensor of the present invention, it is preferable that a surfactant-containing layer containing a surfactant is further formed on the reagent layer. If the surfactant-containing layer is provided in this manner, a hydrophilic film is formed on the surface of the reagent layer, so that the sample and the reagent can be mixed quickly and uniformly. Consequently, a reaction proceeds rapidly, and the repeatability can be improved.

Examples of the surfactant include cationic surfactants, anionic surfactants, ampholytic surfactants, nonionic surfactants, and natural surfactants. Among these, cationic surfactants, nonionic surfactants, and natural surfactants are preferable, and nonionic surfactants and natural surfactants are more preferable. As the natural surfactants, phospholipid can, for example, be used, and lecithin such as egg yolk lecithin, soybean lecithin, hydrogenated lecithin, and high purity lecithin can be used preferably. As the nonionic surfactants, polyoxyethylene sorbitan fatty acid esters such as a product named Tween 20, polyoxyethylene alkyl ether such as a product named Triron X-100, polyoxyethylene phenyl alkyl ether such as a product named Triton X-405 or the like can be used. Among these, phospholipid is particularly preferable, and lecithin such as high purity lecithin is most preferable.

In the biosensor of the present invention, for the electrodes, any electrodes can be used, as long as they can detect electrochemically a reaction between the object to be measured and the sample, and for example, a conductive material can be used. More specifically, gold electrodes, carbon electrodes, silver electrodes, platinum electrodes, and palladium electrodes can be used. Among these, because of excellent electrical conductivity and chemical stability, gold electrodes and carbon electrodes are preferable, and carbon electrodes are more preferable.

In the biosensor of the present invention, there is no particular limitation regarding the reagent, as long as it can react with the object to be measured, and the reaction can be electrochemically detected, but it is preferable that, for example, the reagent contains a redox enzyme. As the enzyme, for example, redox enzymes can be used.

In the biosensor of the present invention, when the enzyme is a redox enzyme, it is preferable that an electron acceptor in a reaction of the enzyme is contained. The redox enzyme can be determined as appropriate, depending on the type of the object to be measured. More specifically, glucose oxidase, pyranose oxidase, glucose dehydrogenase, lactate oxidase, lactate dehydrogenase, fructose dehydrogenase, galactose oxidase, cholesterol oxidase, cholesterol dehydrogenase, alcohol oxidase, alcohol dehydrogenase, bilirubinate oxidase, glucose-6-phosphate dehydrogenase, amino-acid dehydrogenase, formate dehydrogenase, glycerol dehydrogenase, acyl-CoA oxidase, choline oxidase, 4-hydroxybenzoic acid hydroxylase, maleic acid dehydrogenase, sarcosine oxidase, uricase, and the like can be used.

As the electron acceptor, potassium ferricyanide, p-benzoquinone and derivatives thereof, phenazine methosulfate, indophenol, indophenol derivatives such as 2, 6-dichloro phenol indophenol, beta-naphthoquinone-4-sulfonic acid potassium salt, ferrocene, ferrocenes(ferrocene derivatives) such as ferrocenecarboxylic acid, osmium complexes, ruthenium complexes, $NAD^+$, $NADP^+$, pyrroloquinoline quinine (PQQ), methylene blue, and the like can be used. Among these, potassium ferricyanide, ferrocene, osmium complexes, $NAD^+$, $NADP^+$, and the like are preferable. The type and the combination of these reagents can be determined as appropriate, depending on the object to be measured.

In the biosensor of the present invention, there is no limitation regarding the sample to be measured, but the present invention is useful for, for example, samples containing the impurities such as soluble components, insoluble components, solid components, and the like. Examples of the impurities include proteins, lipids, saccharides, and blood cells. Specific examples of the samples include biological samples such as whole blood, blood plasma, blood serum, sputum, urine, and liquor cerebrospinalis, drinks such as juice, foods such as soy sauce and sauce, waste water, rainwater, water for a swimming pool and the like can be used. Among these, whole blood, blood plasma, sputum, liquor cerebrospinalis, and the like are preferable, and whole blood is more preferable.

BEST MODE FOR CARRYING OUT THE Invention

Hereinafter embodiments of the present invention will be described more specifically.
(Embodiment 1)

Figure 1:
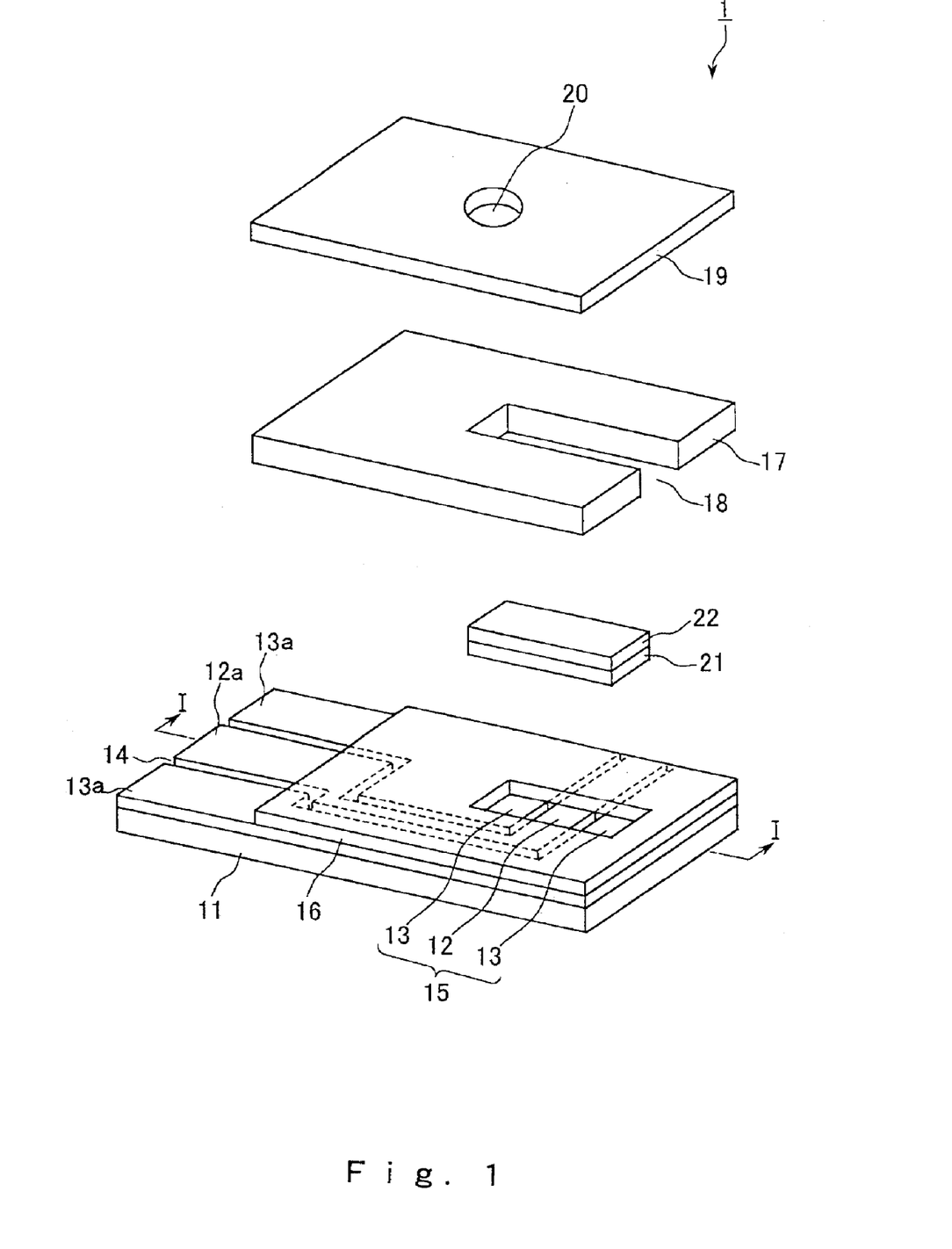
FIG. 1 is a perspective view showing an example of a biosensor of the present invention.
Figure 2:
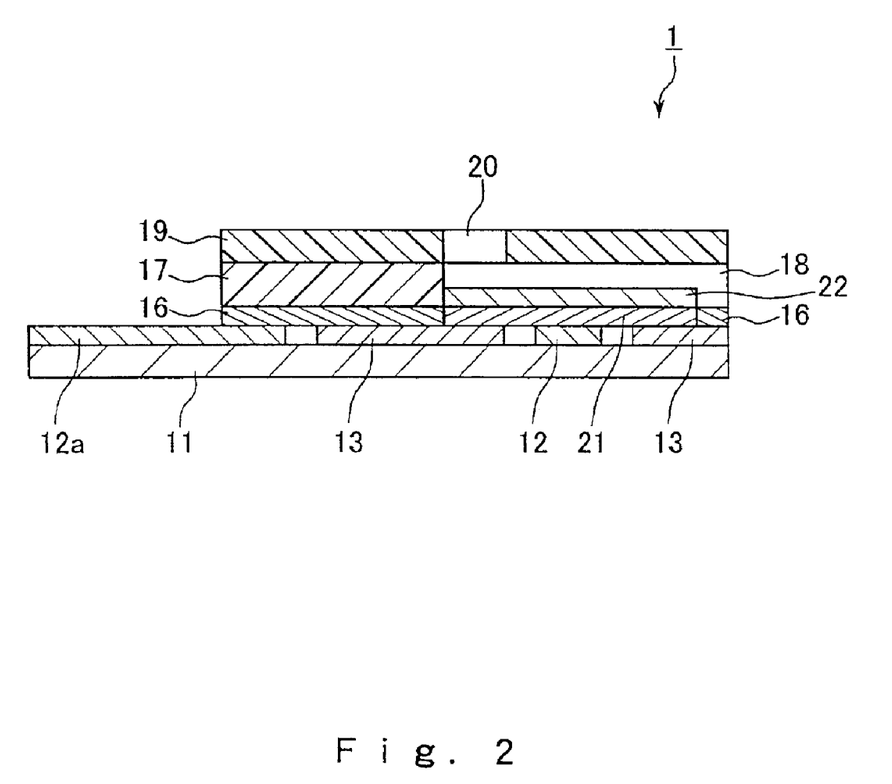
FIG. 2 is a cross-sectional view of the biosensor.

FIGS. 1 and 2 show an example of a biosensor of the present invention. FIG. 1 is a perspective view schematically showing the biosensor, and FIG. 2 is a cross-sectional view taken along line I—I of FIG. 1.

As shown in the drawings, this biosensor 1 includes a substrate 11, an electrode system including a working electrode 12 having a lead portion 12a and two counter electrodes 13 having lead portions 13a, a particulate-containing layer 21, a reagent-containing layer 22, a spacer 17, and a cover 19. A detecting portion 15 is provided on one end portion (on the right side of FIGS. 1 and 2) of the substrate 11, and the two counter electrodes 13 and the working electrode 12 are alternately disposed parallel with the width direction of the substrate 11 on the detecting portion 15. The electrodes drawn out from the detecting portion 15 are disposed on the substrate 11 in such a manner that the electrodes are bent before reaching the lead portions 12a and 13a of the end portion (on the left side of FIGS. 1 and 2). The lead portions 13a, each of which is one end of the counter electrode 13, are disposed on the opposite ends in the width direction in the end portion (on the left side in FIGS. 1 and 2) of the substrate 11, and the lead portion 12a, which is one end of the working electrode 12, is disposed in the center in the width direction. An insulating portion 14 is formed between the working electrode 12 and the counter electrode 13. An insulating layer 16 is formed on such an electrode system, except on the lead portions 12a and 13a and the detecting portion 15. An inorganic particulate-containing layer 21 and the reagent-containing layer 22 are laminated in this order on the detecting portion 15 on which the insulating layer 16 is not formed. A U-shaped spacer 17 having an opening 18 at a portion corresponding to the detecting portion 15 is disposed on the insulating layer 16. A cover 19 having a through-hole 20 at a part of the portion corresponding to the opening 18 is disposed on the spacer 17. In this biosensor 1, a space that is in the opening 18 and is sandwiched by the reagent-containing 22 and the cover 19 serves as a sample supply portion having a capillary structure. The through-hole 20 serves as an air hole for drawing a sample in by capillary phenomenon.

The size of the biosensor 1 is not limited to a particular value, and can be set as appropriate, depending on the amount of a sample to be supplied. For example, the total length can be 15 to 40 mm, the total width can be 5 to 15 mm, the maximum thickness can be 400 to 500 $\mu$m, and the minimum thickness can be 100 to 200 $\mu$m.

The size of the inorganic particulate-containing layer 21 is 5 to 10 mm for the length, 0.5 to 1.5 mm for the width, 0.05 to 5 $\mu$m for the thickness, for example. The size of the reagent-containing layer 22 is 5 to 10 mm for the length, and 0.5 to 1.5 mm for the width, for example. The thickness of the insulating layer 16 is 10 to 50 $\mu$m, for example. The thickness of the spacer 17 is 50 to 200 $\mu$m, for example. The thickness of the cover 19 is 10 to 300 $\mu$m, for example. The diameter of the air hole 20 is 0.5 to 1.5 mm, for example. It should be noted that "length" of each portion refers to the length in the longitudinal direction, and "width" refers to the length in the width direction.

The content of the inorganic particulates in the inorganic particulate-containing layer 21 can be determined as appropriate, depending on the type or the amount of a sample to be supplied, the area of the detecting portion 15 or the like.

For example, when the inorganic particulates are smectite, the content per $cm^2$ preferably is in the range from 0.14 to 14 mg, more preferably in the range from 0.28 to 8.4 mg. When the content per $cm^2$ is 0.14 mg or more, for example, impurities such as blood cells and proteins in blood are prevented from passing through the layer to a higher extent. When the content per $cm^2$ is 14 mg or less, the response speed of the electrodes becomes excellent, and the current sensitivity is further improved.

The amount of the inorganic particulates per $cm^2$ depends on the thickness of the inorganic particulate-containing layer 21, and it is preferable that the thickness of the layer is in the range from 0.05 to 5 $\mu$m, as described above.

The content of the reagent in the reagent-containing layer 22 is not limited to a particular value, and can be determined as appropriate, depending on the type of the reagent, the type or the amount of the sample to be supplied or the like. More specifically, when GOD is used as an enzyme and potassium ferricyanide is used as an electron acceptor, the amount of GOD per $cm^2$ is preferably in the range from 0.2 to 100 U, and more preferably 0.4 to 30 U, and the amount of potassium ferricyanide per $cm^2$ is preferably in the range from 0.4 to 3.6 mg, and more preferably 0.6 to 2.4 mg.

When the amount of potassium ferricyanide per $cm^2$ is 0.4 mg or more, the range in which the glucose concentration can be measured can be broad. When the amount per $cm^2$ is 3.6 mg or less, no cracks occur in the formed reagent-containing layer, and further excellent measurement can be performed.

Such a biosensor 1 can be produced, for example, in the following manner. First, a substrate 11 on which the electrodes and the like are to be formed is prepared. The substrate 11 preferably is formed of an electrically insulating material, such as plastics, glass, paper, and ceramics. Examples of the plastics include polyethylene terephthalate (PET), PS, PMMA, polypropylene (PP), acrylic resin, and glass epoxy.

Next, the electrode system including the working electrode 12 and the counter electrodes 13 is formed on the substrate 11. As the electrodes, gold electrodes, carbon electrodes or the like are preferable, as described above, and the electrodes can be formed by a known method such as coating, screen printing, or an evaporation method, depending on the type thereof.

The gold electrodes can be formed by, for example, an evaporation method, plating, a gold foil attachment method or the like. The evaporation method is a method performed in the following manner, for example. Gold is deposited on a plastic sheet such as PET by, for example, ion plating at a vacuum degree of $1.33 \times 10^{-4}$ Pa, an input power of 300W, a rate of $5\times10^{-1}$ nm/sec (5 Å/sec) for 2 min. Then, the gold foil layer deposited on the sheet is cut in the form of a thin line with a kisscut device. Thus, the cut in the form of a thin line serves as the insulating portion 14, so that the working electrode 12 and the counter electrode 13 can be formed.

Alternatively, carbon electrodes can be formed by, for example, means for screen-printing, coating, or plating carbon ink on the substrate 11.

It is preferable that the surfaces of the electrodes are treated so as to be hydrophilic before a reagent layer 22 as described later is formed on the detecting portion 15. Thus, the surfaces of the electrodes that are hydrophobic are made hydrophilic, which facilitates uniform formation of the reagent layer.

The method for the treatment for hydrophilicity can be determined as appropriate, depending on the type of the electrodes. When the electrodes are gold electrodes, for example, the electrodes can be immersed in a hydrophilic solution such as a mercaptoethanol solution and a mercaptoethanol amine solution, and then are washed and dried.

As a solvent for the hydrophilic solution, for example, organic solvents such as ethanol, butanol, acetone, and tetrahydrofuran can be used. The concentration of the hydrophilic solution is, for example, in the range from 0.01 to 100 mmol/L, preferably 0.05 to 50 mmol/L. For washing, organic solvents, such as ethanol, methanol, butanol, acetone, and tetrahydrofuran, and washing solutions such as purified water can be used, for example.

In the case where the electrodes are carbon electrodes, the treatment for hydrophilicity can be performed by, for example, immersing the electrodes in a surfactant and then washing them with purified water.

Next, the insulating layer 16 is formed on the substrate on which the electrode system is formed. The insulating layer 16 can be formed by, for example, printing an insulating paste on the electrodes, and subjecting it to a heat treatment.

The insulating paste can be prepared by, for example, dissolving an insulating resin in a solvent. Examples of the insulating resin include polyester, butyral resin, and phenolic resin. Examples of the solvent include carbitol acetate, and dibasic acid esters (DBE solvent). The concentration of the insulating resin in the paste is preferably in the range from 65 to 100 wt %, and more preferably 75 to 90 wt %, and particularly preferably in the range from 80 to 85 wt %.

Furthermore, in addition to the printing as described above, the insulating layer 16 can be formed by coating, film attachment, etching or other methods.

Next, the inorganic particulate-containing layer 21 is formed on the detecting portion 15 on which the insulating layer 16 has not been formed. This layer can be formed by, for example, preparing a dispersion system in which inorganic particulates are dispersed, pouring the dispersion system into the detecting portion 15 and drying it.

It is preferable to stir the dispersion system for one hour or more, more preferably 5 hours or more, to prevent the dispersed inorganic particulates from settling. For the same reason, it is preferable to continue stirring during use. Examples of the dispersion medium of the dispersion system include water, alcohol, N,N-dimethylformamide (DMF), and dimethylsulfoxide (DMSO). Among these, ultrapure water is preferable. There is no limitation regarding the concentration of the inorganic particulates in the dispersion system.

There is no particular limitation regarding the means for drying. For example, natural curing, air drying, drying under reduced pressure, lyophilization under reduced pressure or the like can be used. These methods can be combined. As the conditions for this treatment, the temperature is preferably in the range from 4 to 60° C., and the relative humidity is preferably in the range from RH 5 to 40%.

Next, the reagent-containing layer 22 is formed on the inorganic particulate-containing layer 21.

The reagent-containing layer 22 can be formed by preparing a solution containing the reagent, pouring the solution onto the inorganic particulate-containing layer 21, and drying it. As the reagent, those described above can be used.

The solution can be prepared by dissolving the reagent in a solvent. There is no particular limitation regarding the solvent. For example, water, buffers, or organic solvents such as ethanol, methanol, butanol, dimethylsulfoxide (DMSO) and tetrahydrofuran can be used. Examples of the buffer include phosphate buffer, citrate buffer, acetate buffer, Tris-HCl buffer, and Good's buffer. The pH thereof is preferable in the range from 4 to 9, more preferably 5 to 8. Examples of the water include purified water, distilled water, and ultrapure water. Among these, ultrapure water is preferable, because a biosensor that hardly contains impurities and has a high precision can be produced.

There is no limitation regarding the concentration of the reagent in the solution. For example, in the case of an enzyme, the concentration is preferably in the range from 10 to 10,000KU/L, more preferably 50 to 5000KU/L. In the case where an electron acceptor is contained, the concentration is preferably in the range from 0.01 to 10 mol/L, and more preferably 0.05 to 5 mol/L.

There is no limitation regarding the method for pouring the solution onto the inorganic particulate-containing layer 21, and for example, the method can be performed with an automatically driven dispenser or the like.

The amount of the solution to be poured can be determined as appropriate, depending on the size of the reagent-containing layer to be formed, the content of the reagent, the amount of the sample or the like.

There is no limitation regarding the means for drying the poured solution. For example, natural curing, air drying, drying under reduced pressure, lyophilization under reduced pressure or the like can be used. These methods can be combined.

In the case of hot air drying as the conditions, for example, the temperature is in the range from 10 to 60° C., the relative humidity is in the range from RH 5 to 40%, and the time is in the range from 1 to 30 minutes.

Next, the spacer 17 is disposed on the insulating layer 16. As shown in the drawings, the spacer 17 has the opening 18 at the portion corresponding to the reagent-containing layer 22.

The spacer 17 can be made of, for example, a resin film, or a resin tape. If it is a two-faced tape, the cover as described later can be attached easily. In addition to that, the spacer can, for example, be formed by resist printing or other means.

Next, the cover 19 is disposed on the spacer 17. There is no limitation regarding the material of the cover 19. For example, various plastics can be used, and preferably transparent resin such as PET can be used.

It is preferable that the thus produced biosensor 1 is stored air-tightly together with a desiccant such as molecular sieves, silica gel, and calcium oxide in order not to be affected by humidity, when it is stored for a long time. The biosensor 1 can be used in combination with measuring equipment provided with, for example, means for applying a predetermined voltage for a certain time, means for measuring an electrical signal transmitted from the biosensor, means for calculating the electrical signal into the concentration of the object to be measured and other means.

The use of the biosensor 1 will be described by taking an example in which a sample is whole blood, the object to be measured is glucose, and the reagents are GOD and potassium ferricyanide.

First, the whole blood sample is brought into contact with one end of the opening 18 of the biosensor 1. This opening 18 has a capillary structure, as described above, and the through-hole 20 is provided in the cover 19 at the portion corresponding to the other end thereof, so that the sample is drawn in by the capillary phenomenon. The drawn sample permeates the reagent-containing layer 22 provided on the detecting portion 15. Then, the sample dissolves GOD and potassium ferricyanide in the reagent-containing layer 22, and these reagents react with glucose in the sample. The glucose in the sample is oxidized by the GOD, and the potassium ferricyanide is reduced by electrons that have been moved by the oxidation reaction, so that potassium ferrocyanide (ferrocyanide ions) is produced.

This reaction solution reaches the inorganic particulate-containing layer 21, which is the underlying layer, permeates rapidly between aggregates of the inorganic particulates, and reaches the electrode surface while swelling the inorganic particulates without applying an excessive thermodynamic burden. On the other hand, the impurities such as blood cells contained in the reaction solution cannot pass between the swollen inorganic particulates, so that they are retained in the inorganic particulate-containing layer 21 and are prevented from being adsorbed in the electrode surface.

Then, after a predetermined time has passed since the supply of the blood sample, a voltage is applied between the counter electrodes 13 and the working electrode 12 by means for applying the voltage, so that the reduced potassium ferrocyanide (ferrocyanide ions) that is in contact with the electrodes is oxidized electrochemically into potassium ferricyanide, and the oxidation current at that time is detected by means for measuring the electrical signal via the lead portion 12a of the working electrode 12. The peak value of the oxidation current is proportional to the glucose concentration in the sample, so that the glucose concentration in the sample can be obtained by converting the oxidation current to the glucose concentration by the calculating means.

According to such a biosensor, the impurities in the sample cannot be adsorbed in the electrodes, as described above, so that the sensitivity is prevented from being deteriorated, and measurement can be performed with high precision.

In the biosensor 1, for example, the reagent-containing layer 22 may further contain the water-insoluble particulates as described above. The content of the water-insoluble particulates in the reagent-containing layer can be determined as appropriate, depending on the type thereof, the type or the amount of the sample or the like.

Such an inorganic particulate-containing layer containing water-insoluble particulates can be formed by preparing a solution containing the reagents and the water-insoluble particulates in the same manner as described above.

In this embodiment, an example of a biosensor for measuring glucose has been shown, but the present invention is not limited thereto. For example, the reagent can be determined as appropriate, depending on the object to be measured. More specifically, for example, lactate oxidase for a biosensor for lactic acid, alcohol oxidase for a biosensor for alcohol, cholesterol oxidase for a biosensor for cholesterol or the like can be used. For a biosensor for glucose, pyranose oxidase or glucose dehydrogenase can be used, for example.

(Embodiment 2)

Figure 3:
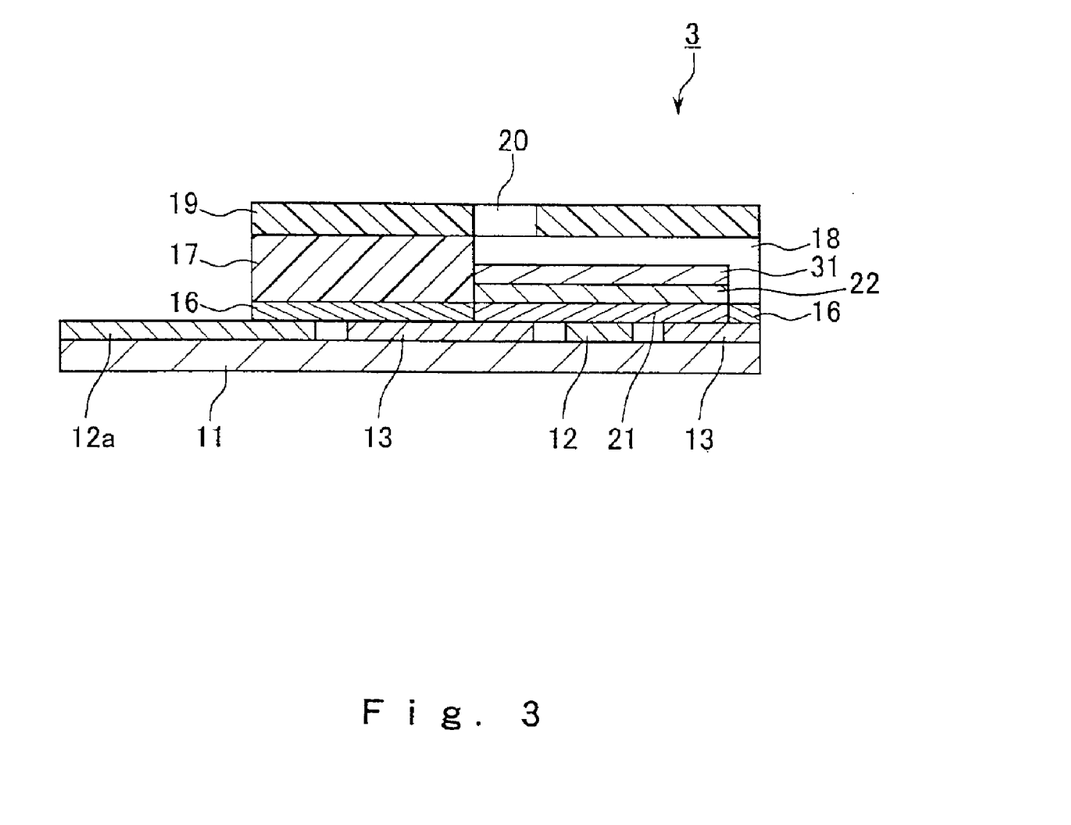
FIG. 3 is a cross-sectional view showing another example of a biosensor of the present invention.

This embodiment is an example of the biosensor of the present invention having a surfactant-containing layer on the reagent-containing layer. FIG. 3 is a cross-sectional view of this biosensor. In FIG. 3, the same components as those in FIG. 2 bear the same reference numeral.

As shown in FIG. 3, the biosensor 3 has the same structure as in Embodiment 1, except that a surfactant-containing layer 31 is laminated on the reagent-containing layer 22. Thus, if the surfactant-containing layer 31 is provided, not only can the sample and the reagents be mixed rapidly and uniformly, but also the sample liquid in the capillary structure can be drawn in more rapidly and more reliably.

The content of the surfactant in the surfactant-containing layer 31 can be determined as appropriate, depending on the type or the amount of the sample to be supplied, the type of the surfactant or the like.

The surfactant-containing layer 31 can be formed by, for example, preparing a solution containing the various surfactants as described above, pouring the solution onto the reagent-containing layer 22, and drying it. There is no limitation regarding the concentration of the surfactant-containing layer. For example, the concentration is preferably in the range from 0.1 to 1.0 wt %, more preferably 0.3 to 0.6 wt %. As a solvent for the solution, 1-butanol, 2-butanol, toluene, ethanol, methanol, DMF, DMSO or the like can be used. More specifically, when egg yolk lecithin is used as the surfactant, it is preferable that 1-butanol is used as the solvent, and the concentration of the surfactant is in the range from 0.3 to 0.5 wt %.

EXAMPLES

Example 1

A biosensor for measuring glucose having the same structure as that shown in FIG. 3 was produced in the following manner.

First, a PET sheet (manufactured by Toray Industries. Inc.) was prepared as the substrate 11, and a carbon electrode system including a working electrode and counter electrodes, each of which had a lead portion, was formed on one surface thereof. The carbon electrodes were formed by patterning by screen printing.

Next, an insulating resin polyester was dissolved in the solvent carbitol acetate so that the concentration was 75 wt % to prepare insulating paste, and the insulating paste was screen-printed on the electrode system. The printing was performed under the conditions: 300 mesh screen; and a squeegee pressure of 40 kg, and the amount used for the printing was 0.002 mL per $cm^2$ of the electrode area. Printing was not performed on the detecting portion 15 and the lead portions 12a and 13a. Then, a heat treatment was performed, and thus the insulating layer 16 was formed. The heat treatment was performed at a temperature of 90° C. for 60 min.

Then, the inorganic particulate-containing layer 21 was formed on the detecting portion 15 on which the insulating layer 16 was not formed. First, a dispersion system (having a concentration of 0.2 wt %) in which smectite (product name Labnight XLG; Laboat Industries Co.) was dispersed in purified water was prepared, and 4 μl of the dispersion system was dispensed into the detecting portion 15. Then, immediately after that, a drying treatment was performed at 50° C. for 10 minutes, and thus the inorganic particulate-containing layer 21 was formed.

Furthermore, the reagent-containing layer 22 was formed on the inorganic particulate-containing layer 21. First, GOD and potassium ferricyanide were added to purified water, and stirred at room temperature so that a reagent solution in which they were dissolved completely was prepared. The concentration of the GOD was 5000 U/mL and the concentration of the potassium ferricyanide was 3 wt %. Then, 2 μL of the reagent solution was dispensed on the inorganic particulate-containing layer 21, and a drying treatment was performed at 50° C. for 10 minutes, and thus the reagent-containing layer 22 was formed.

Next, the surfactant-containing layer 31 was formed on the reagent-containing layer 22. This was performed in the following manner. Egg yolk lecithin was dissolved in 1-butanol so that the concentration was 0.5 wt % to prepare a lecithin solution, and 2 μL of the lecithin solution was dripped on the reagent-containing layer 22, and thus the surfactant-containing layer 31 was formed.

A PET spacer 17 (manufactured by Sony Chemicals Corporation) having an opening 18 at the portion corresponding to the surfactant-containing layer 31 was disposed on the insulating layer 16. Furthermore, a PET cover 19 (manufactured by Toray Industries. Inc.) having a through-hole 20 serving as an air hole was disposed on the spacer, and thus a biosensor was produced.

Comparative Example 1

A biosensor for measuring glucose was produced in the same manner as in Example 1 except for the following. Instead of forming the inorganic particulate-containing layer 21 on the detecting portion 15 with smectite, 4 μl of a 0.25 wt % carboxy methyl cellulose solution was dripped, and a drying treatment was performed at 50° C. for 10 minutes, and thus a water absorptive high molecular weight layer was formed.

The biosensors of Example 1 and Comparative Example 1 produced in the above-described manner were tested in regard to the following respects.
(Measurement of Current of a Glucose Solution)

Figure 4:
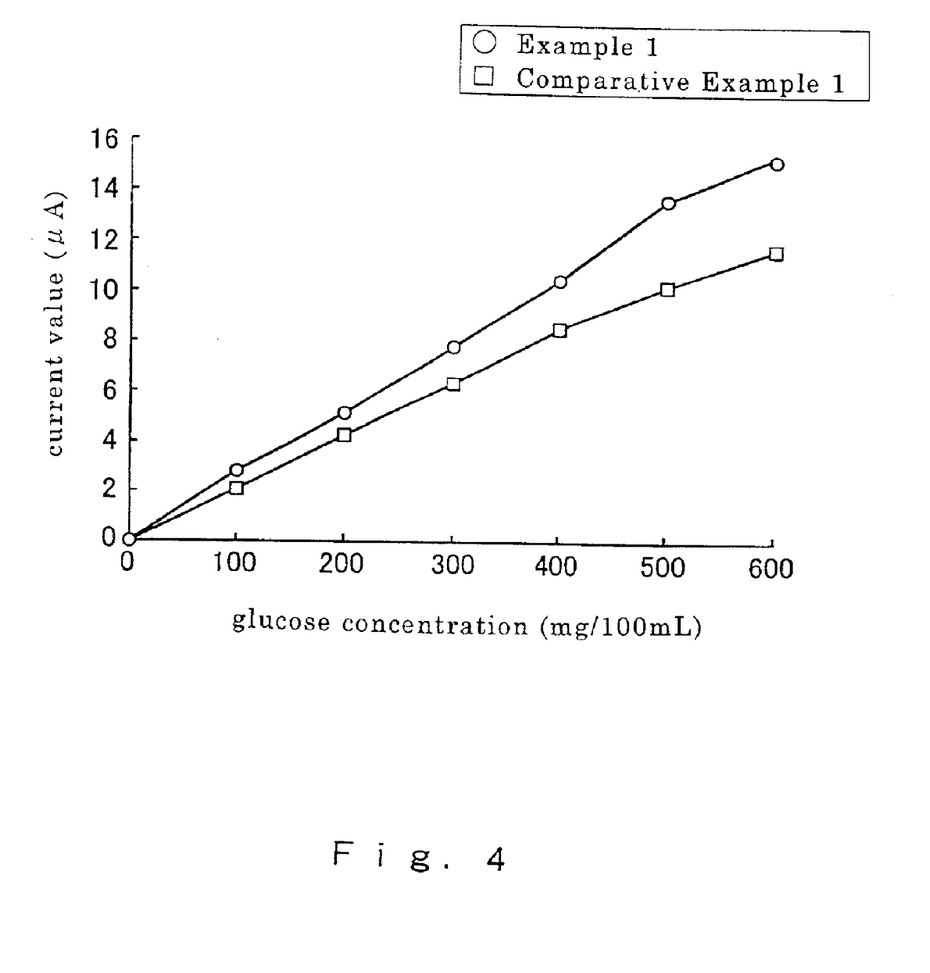
FIG. 4 is a graph showing the relationship between the glucose concentration and the current value in an example of the present invention.

Glucose solutions having predetermined concentrations (100, 200, 300, 400, 500, and 600 mg/100 mL) were prepared to be used as sample liquids. About 2 μL of the sample liquid was drawn in by the capillary phenomenon from the opening of each biosensor, and a reaction was effected for 25 seconds. Then, the current value was measured at the time when a voltage of 500 mV was applied for 5 seconds, using Potentiostat CV-50W (product name, manufactured by BAS Co. Ltd.). FIG. 4 shows the results. In FIG. 4, ○ indicates the results of the biosensor of Example 1, and □ indicates the results of the biosensor of Comparative Example 1.

As shown in FIG. 4, the biosensor of Example 1 provides a current value about 1.2 times higher than that provided by the biosensor of the comparative example, and exhibits a highly correlated relationship between the current and the glucose concentration.
(Influence of Hematocrit on the Biosensor)

Figure 5:
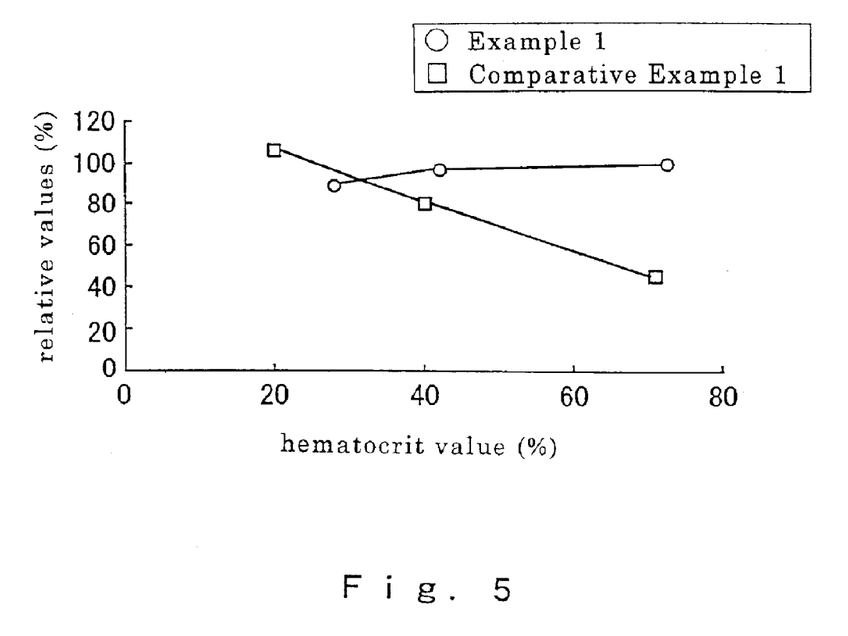
FIG. 5 is a graph showing the relationship between the hematocrit value and the current value in the example.

A whole blood sample having a hematocrit value of 42% and a glucose concentration of 125 mg/100 mL was separated into blood cells and blood plasma by centrifugation, and they were mixed so that the hematocrit value of the sample liquid became a predetermined value (Ht 20%, 25%, 42%, and 70%). Then, the current with respect to each sample was measured in the same manner as above. FIG. 5 shows the results in which the measured values are indicated by relative values (%) with respect to the current value of the sample having a hematocrit (Ht) of 42% obtained by the biosensor of Example 1 as 100%. In FIG. 5, ○ indicates the results of the biosensor of Example 1, and □ indicates the results of the biosensor of Comparative Example 1.

As shown in FIG. 5, the biosensor of Example 1 provides a substantially constant measured value, because it is not affected by erythrocytes or the like even if the hematocrit value of the sample is changed. On the other hand, according to the biosensor of Comparative Example 1, the current decreases, as the hematocrit value increases, so that the measurement precision dropped.

Example 2

A biosensor for measuring glucose was produced in the same manner as in Example 1, except that a dispersion aqueous system (0.2 wt %) of expansive sodium tetrasilicon fluoride mica (product name Na-TS; manufactured by TOPY INDUSTRIES LIMITED) was used, instead of the dispersion system of smectite.

The glucose in the whole blood samples was measured, using the biosensors of Examples 1 and 2 and Comparative Example 1.

As the samples, whole blood having a hemacrit value of 48% was used, and the current was measured in the same manner as above. As a control, blood plasma obtained by centrifuging the same whole blood was prepared, and the current with respect to this control was measured. All the whole blood samples and the plasma sample as the control were prepared so as to have a glucose concentration of 93 mg/100 mL. The obtained current value was substituted in the following equation to obtain a relative value (%) with respect to the current value of the control as 100%. As the relative value (%) is close to 100%, the sample is regarded as being less affected by blood cells. Table 1 shows the results.

Relative value(%)=100×(Y−X)/Y

X: current value of a whole blood sample
Y: current value of a control

TABLE 1

| | Material | Relative value (%) |
|---|---|---|
| Example 1 | expansive mica | 87.2 |
| Example 2 | smectite | 91.8 |
| Comparative Example 1 | CMC | 78.0 |

As shown in Table 1, in the biosensors of Examples 1 and 2, the relative values are high, and the current values are close to that of the control.

These results indicate that the biosensors of the examples containing the inorganic particulates can measure with high precision without being affected by the difference in the properties between samples, such as hematocrit values.

INDUSTRIAL APPLICABILITY

According to the biosensor of the present invention, since the reagent layer contains inorganic particulates, impurities such as erythrocytes are prevented from becoming attached to the electrodes. Therefore, the object to be measured in a sample can be measured rapidly, simply and highly precisely. Thus, the biosensor of the present invention is useful in, for example, the field of clinical medicine.

What is claimed:

1. A biosensor comprising a substrate, a reagent layer containing a reagent, and an electrode system including a working electrode and a counter electrode, the electrode system being disposed on the substrate, and the reagent layer being formed on the electrode system, wherein the reagent layer further comprises expansive inorganic particulates and is a laminate comprising a reagent-containing layer containing the reagent and a particulate-containing layer containing the expansive inorganic particulates.

2. The biosensor according to claim 1, wherein the expansive inorganic particulate-containing layer is present between the reagent-containing layer and the electrode system.

3. The biosensor according to claim 1, wherein the reagent layer contains aggregates of expansive inorganic particulates.

4. The biosensor according to claim 1, wherein a layer containing expansive inorganic particulates is formed by applying a dispersion solution in which the expansive inorganic particulates are dispersed on the electrodes, and drying the dispersion solution.

5. The biosensor according to claim 1, wherein the expansive inorganic particulates are particulates of clay mineral.

6. The biosensor according to claim 5, wherein the clay mineral is expansive phyllosilicate.

7. The biosensor according to claim 6, wherein the expansive phyllosilicate is at least one of smectite and expansive mica.

8. The biosensor according to claim 7, wherein the smectite is at least one selected from the group consisting of hectorite, saponite, and montmorillonite.

9. The biosensor according to claim 7, wherein the expansive mica is at least one of sodium tetrasilicon fluoride mica and teniorite.

10. The biosensor according to claim 1, wherein the content of the expansive inorganic particulates in the layer containing expansive inorganic particulates is in a range from 0.14 to 14 mg per cm$^2$ of an area.

11. The biosensor according to claim 1, wherein the thickness of the layer containing expansive inorganic particulates is in a range from 0.05 to 5 $\mu$m.

12. The biosensor according to claim 1, wherein the reagent layer further comprises particulates of a water-insoluble high molecular weight compound.

13. The biosensor according to claim 12, wherein the water-insoluble high molecular weight compound is a polymer or a copolymer containing at least one of acrylic acid, methacrylic acid, maleic acid, acrylic ester, methacrylic acid ester, maleic acid ester, styrene, and styrene derivative monomer, or a polyamide-based high molecular weight compound.

14. The biosensor according to claim 12, wherein the average particle diameter of the particulates of the water-insoluble high molecular weight compound is in a range from 0.1 to 45 $\mu$m.

15. The biosensor according to claim 1, further comprising a layer containing particulates of a water-insoluble high molecular weight compound, the reagent layer being formed between the electrode system and the layer containing particulates of a water-insoluble high molecular weight compound.

16. The biosensor according to claim 1, wherein a surfactant-containing layer containing a surfactant further is formed on the reagent layer.

17. The biosensor according to claim 1, wherein the electrodes are at least one selected from the group consisting of gold electrodes, carbon electrodes and silver electrodes.

18. The biosensor according to claim 1, wherein the reagent contains a redox enzyme.

19. The biosensor according to claim 1, wherein the reagent contains a redox enzyme and an electron acceptor in a reaction of the enzyme.

20. The biosensor according to claim 1, wherein the sample to be measured is blood.

* * * * *